United States Patent
Chelvayohan et al.

(10) Patent No.: US 6,360,582 B1
(45) Date of Patent: Mar. 26, 2002

(54) METHOD FOR CALIBRATION OF CHEMICAL SENSOR IN MEASURING CHANGES IN CHEMICAL CONCENTRATION

(75) Inventors: Mahesan Chelvayohan, Lexington; Patrick L. Kroger, Versailles, both of KY (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 09/484,829

(22) Filed: Jan. 18, 2000

(51) Int. Cl.⁷ .................. G01N 21/01; G01N 27/00; G01N 21/35
(52) U.S. Cl. ............... 73/23.2; 73/23.21; 73/31.01; 73/61.48; 73/1.03; 73/1.06; 250/339.09; 250/339.13; 250/343
(58) Field of Search ............... 73/23.2, 23.21, 73/23.23, 23.3, 31.01, 31.02, 61.41, 61.44, 61.48, 64.43, 1.02, 1.03, 1.06; 250/343, 339.09, 339.12, 339.13

(56) References Cited

U.S. PATENT DOCUMENTS

| | | | | |
|---|---|---|---|---|
| 2,984,988 A | * | 5/1961 | Berger et al. ................. 62/24 |
| 3,281,596 A | * | 10/1966 | Williston .................. 250/43.5 |
| 3,975,727 A | * | 8/1976 | Mader et al. ........ 340/347 NT |
| 4,526,028 A | * | 7/1985 | Hübner ......................... 73/23 |
| 5,065,613 A | * | 11/1991 | Lehnert et al. ............. 73/23.2 |
| 5,184,500 A | * | 2/1993 | Krema et al. .............. 73/23.2 |
| 5,507,173 A | * | 4/1996 | Shearer et al. ............. 73/23.2 |
| 5,514,968 A | * | 5/1996 | Spanjers .................. 205/782.5 |
| 5,553,616 A | * | 9/1996 | Ham et al. ................. 128/633 |
| 5,559,728 A | * | 9/1996 | Kowalski et al. ....... 364/571.02 |
| 5,591,975 A | * | 1/1997 | Jack et al. ................ 250/338.5 |
| 5,818,048 A | * | 10/1998 | Sodickson et al. .......... 250/343 |
| 5,866,430 A | * | 2/1999 | Grow ......................... 436/172 |
| 6,035,246 A | * | 3/2000 | Wagner ...................... 700/266 |
| 6,067,840 A | * | 5/2000 | Chelvayohan et al. ....... 73/23.2 |
| 6,094,968 A | * | 8/2000 | Scheufler et al. ........... 73/23.2 |
| 6,114,700 A | * | 9/2000 | Blades ....................... 250/343 |
| 6,157,041 A | * | 12/2000 | Thomas et al. ............ 250/573 |

OTHER PUBLICATIONS

U.S. Application Serial No. 09/386,084 entitled Combustion Chamber Leak Detection for Fossil Fuel Fired Apparatus and Method Therefor filed Aug. 30, 1999 Rowlette et al.
U.S. Application Serial No. 09/088,138 entitled Method and Apparatus for Infrared Sensing of Gas filed Jun. 1, 1998 Chelvayohan, M. et al. Now US Pat. No. 6067840.

* cited by examiner

Primary Examiner—Hezron Williams
Assistant Examiner—David J. Wiggins
(74) Attorney, Agent, or Firm—Russell E. Baumann; Frederick J. Telecky, Jr.

(57) ABSTRACT

Changes in the concentration of a chemical, such as a gas, are determined using a non-linear chemical sensor which is subject to shifts in calibration over time. In order to minimize errors caused by such shifts in calibration a first infrared signal ($I_g(1)$) is measured and using an absorption value under an assumed chemical concentration ($C(1)$), a zero chemical signal $I_o(1)$ is calculated using the known physical law and mathematical relation Absorption=$1-I_g/I_o$. A second infrared signal ($I_g(2)$) is then measured and the absorption value is calculated using the previously calculated zero chemical signal. A second concentration ($C(2)$) is then determined and the change in concentration is calculated by subtracting $C(2)$ from $C(1)$.

7 Claims, 2 Drawing Sheets

METHOD FOR CALIBRATION OF CHEMICAL SENSOR IN MEASURING CHANGES IN CHEMICAL CONCENTRATION

FIELD OF THE INVENTION

This invention relates generally to chemical sensing and more particularly to the sensing of changes in concentration of a selected chemical, such as $CO_2$, using non-linear sensors to detect changes in attenuation of an optical beam being transmitted through a medium potentially containing some of a such selected chemical, such as infrared sensors.

BACKGROUND OF THE INVENTION

Absolute measurements and accuracy are generally of interest in many chemical sensing applications. However, in certain applications the change (delta) that occurs in the chemical concentration during a process is of more interest than the absolute value. Among the chemical sensor technologies currently available, some of them are inherently linear in nature (e.g., electrochemical) and some are non-linear (e.g., infrared and metal oxide). In the non-linear sensors, the non-linear measured parameter is converted linearly using appropriate electronics/software. For example, in infrared sensors, the measured parameter, infra-red absorption, increases as in FIG. 1 with concentration. Knowing this curve shape, instruments are designed to linearize the output, mostly by software. The curve information is stored in the sensor microprocessor during calibration and used during the linearization routine.

Delta measurements are directly related to the slope of the measured parameter vs. concentration curve (example shown in FIG. 1). For small changes in concentration, Change in Concentration (Delta)=Slope×Change in the measured absorption parameter.

In non-linear sensors, since the slope changes with the concentration, the delta measurement will be accurate only if the absolute concentration is known accurately. Normally, chemical sensors often tend to drift over time and need to be calibrated periodically to maintain accuracy. In some applications (for example, residential applications), re-calibration of a chemical sensor is not very feasible. In a drifted sensor, the absolute concentration measured and hence the slope used at that concentration will not be accurate. This will cause the delta measurement also to be inaccurate. The more the sensor drifts, the more the inaccuracy in delta measurement. So in situations where calibration is not feasible, the error in the delta measurement can become unacceptably high.

In gas furnace heat exchanger leak detection for example, the $CO_2$ level is measured in the air-side of the furnace just before and after the furnace is fired. If the furnace heat exchanger has a leak, the $CO_2$ level will increase significantly. A threshold is normally set on this delta $CO_2$ value to set an alarm and shut off the furnace. The delta measurement will be accurate only if the sensor is calibrated and holds its calibration during the measurement. Since gas sensors are normally prone to some degree of drifting and hence the delta measurement, over time, will not be accurate. On the other hand, furnace manufacturers expect the leak detection to last for 10 years or more and re-calibration is not a practical alternative.

SUMMARY OF THE INVENTION

It is an object of the present invention to provide a method for measuring the change in concentration of a selected chemical, such as a selected gas, which measurement has reduced error caused by calibration changes in the chemical sensor over time. Another object is the provision of a method for measuring a change in concentration of $CO_2$ in a gas furnace leak detection application which has improved accuracy over an expected life without re-calibration of the sensor used in performing the measurements. Yet another object of the invention is to overcome the above noted prior art limitations.

Briefly described, a method for sensing the change in concentration of a selected chemical, such as the gas $CO_2$, according to the invention comprises the steps of measuring a first infrared signal $I_g(1)$ by means of a suitable gas sensor such as an NDIR (non-dispersive infrared sensor), using the relation: absorption=$1-I_g/I_o$ where $I_g$ is the infrared signal and $I_o$ is the zero gas, or base line, signal, using the absorption value under a preselected gas concentration $C(1)$ calculating the corresponding $I_o(1)$ value, then measuring a second infrared signal $I_g(2)$, calculating a new absorption value using the calculated $I_o(1)$ value for $I_o$ and respective concentration $C(2)$ and subtracting the first concentration $C(1)$ from the second concentration $C(2)$ to obtain the change in concentration. By choosing the preselected gas concentration $C(1)$ to be intermediate to two extremes, the divergence of a drifted sensor can be limited to an acceptable level.

BRIEF DESCRIPTION OF THE DRAWINGS

Other objects, advantages and details of the new and improved method of the invention appear in the following detailed description of the preferred embodiment of the invention, the detailed description referring to the drawings in which.

DETAILED DESCRIPTION OF THE PREFERRED EMBODIMENT

Figure 3:
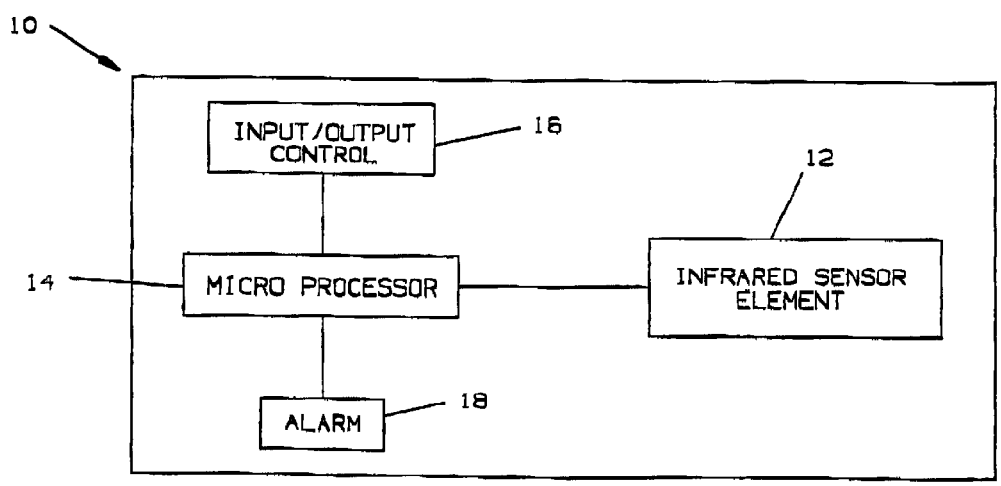
FIG. 3 is a schematic block diagram of a measuring system employing the method of the invention.

In gas furnace heat exchanger leak detection, the $CO_2$ level is measured on the air-side of the furnace just before and after the furnace is fired. As seen in the control system 10 shown in FIG. 3, infrared sensor element 12, used to measure the $CO_2$ level, is coupled to microprocessor 14, in turn coupled to an input/output control 16 and an alarm 18. If the furnace heat exchanger has a leak, the $CO_2$ level will increase significantly. A threshold is normally set on this delta $CO_2$ value to set the alarm and shut off the furnace. A leak detection system for gas furnaces of this type is shown and described in copending, commonly assigned U.S. application Ser. No. 09/386,084. Further, suitable NDIR sensors are shown and described in copending, coassigned U.S. application Ser. No. 09/088,138. The subject matter of these applications are included herein by this reference.

The delta measurement obtained using such a system will be accurate only if the sensor is calibrated and holds its calibrations during the measurement. As noted above, gas sensors are normally prone to some degree of drifting and hence the delta measurement over time will not be accurate. The furnace manufacturers expect the leak detection to last for 10 years or more and do not want to calibrate them after installation.

Infrared sensors measure the infrared signal under the gas to be measured (in this case $CO_2$) and calculate the absorption and hence the concentration of the gas using the calibration values. The calibration values of a typical infrared sensor are the zero gas signal $I_o$ (base line) and an absorption concentration curve (absorption curve). Under the gas to be measured, the sensor measures the infrared signal $I_g$ and calculates the absorption using the relation:

$$Absorption = 1 - I_g/I_o$$

By applying the measured absorption to the absorption curve the sensor system calculates the gas concentration. If the sensor loses its baseline calibration (zero calibration), the measured absorption and hence the calculated concentration will not be correct. For example, if $I_o$ drifts low, the sensor would not know about this and will use a higher $I_o$ value in the calculation. This will result in a higher absorption value and hence a higher ppm value than the actual concentration.

Figure 1:
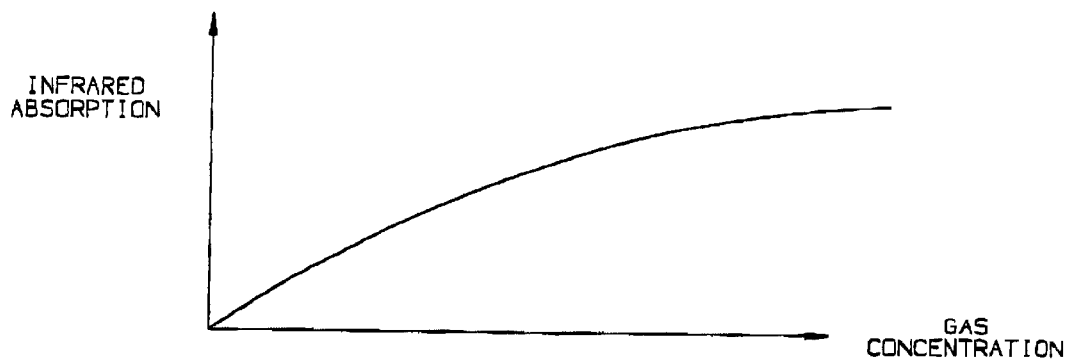
FIG. 1 is a graph of infrared absorption vs. gas concentration of a selected gas, such as $CO_2$.
Figure 2:
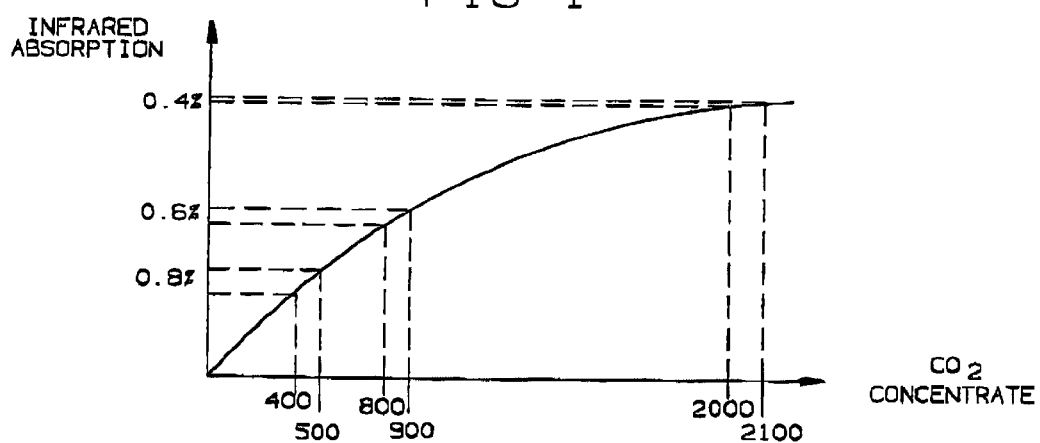
FIG. 2 is a graph similar to FIG. 1 but showing infrared absorption values related to changes in $CO_2$ concentration.

In a delta $CO_2$ measurement mode the sensor measures two $CO_2$ measurements. In a baseline-drifted sensor the measured $CO_2$ levels will be incorrect in both instances. The error on the delta measurement can be significantly high due to the non-linear nature of the curve, as demonstrated by the following example. FIG. 2 shows that a 100 ppm delta will introduce 0.8% change in absorption at 400 ppm level and 0.6% and 0.4% at 800 and 2000 ppm levels respectively. If the sensor has drifted, and it reads 400 ppm as 800 ppm, a 100 ppm delta will introduce 0.8% absorption change. Since the sensor thinks the gas level is 800 ppm it will apply the 0.6%/100 ppm slope and calculate the delta as 133 ppm. Similarly, if the drift were severe and it reads 400 ppm as 2000 ppm, a 100 ppm delta will be measured as 200 ppm delta using the 0.4%/100 ppm slope. This example demonstrates that if the sensor drifts significantly over a period of time, it can cause unacceptable error in the delta measurements. The error in the delta measurement is clearly a function of the base line drift. If the drift is more, the error would be more and has no theoretical boundaries.

In accordance with the invention, a method of forced calibration is used to limit the maximum error the delta measurement can have. In the method of forced calibration, the sensor assumes that the first $CO_2$ measurement $C(1)$ is a set value, for example, 800 ppm. The sensor will then measure the delta absorption and use the fixed slope, 0.6%/100 ppm in this example for delta $CO_2$ calculation. In a normal home environment, the $CO_2$ concentration lies between 400 and 2000 ppm. In the worst case scenario the sensor will be forced calibrated to 800 ppm while the actual gas concentration is either 400 or 2000 ppm. In both of these cases a 100 ppm delta would be measured as 0.8*100/0.6= 133 ppm and 0.4*100/0.6=66 ppm. In the forced calibration method the error in the delta measurement is limited by the fact that the indoor ambient $CO_2$ level is limited by nature. The assumption made here, that the absorption characteristics of the system (filters, optical path, etc.) has not changed, is normally true. As explained above, this forced calibration scheme is limits the error on delta measurement as long as the sensor operates electronically.

Consider a simple $CO_2$ sensor. When the sensor was originally calibrated it would have stored the $I_o$ value and the absorption curve (absorption vs. concentration information) in the memory of microprocessor 14. Using a conventional procedure during a gas measurement, the sensor measures the infrared signal $I_g$ and calculates the absorption using the relation, $A=1-I_g(1)/I_o$. Then using the absorption curve it will predict the concentration of the gas present. Over a period of time the $I_o$ value can change and the sensor will not know this value unless it is calibrated again.

In accordance with the forced calibration method of the invention, when the sensor is used to measure a delta measurement the sensor is forced to use the $CO_2$ concentration $C(1)$ at 800 ppm during the first gas measurement. So, the sensor measures the signal $I_g(1)$ and using the absorption value under 800 ppm $CO_2$, $A(1)$ from the absorption curve it will calculate the new $I_o$ value ($I_o(1)$) using the equation;

$$A(1)=1-I_g(2)/I_o(1)$$

So the forced calibration is helping the instrument to pick a reasonable $I_o$ value. When it takes the second measurement, it will measure the signal $I_g(2)$ and will calculate the new absorption using the relation, $$A(2)=1-I_g(2)/I_o(1)$$

It will then calculate the gas concentration $C(2)$, corresponding to this new absorption, using the absorption curve (from the memory of microprocessor 14). The resulting delta concentration is $C(2)-800$ ppm.

Figure 4:
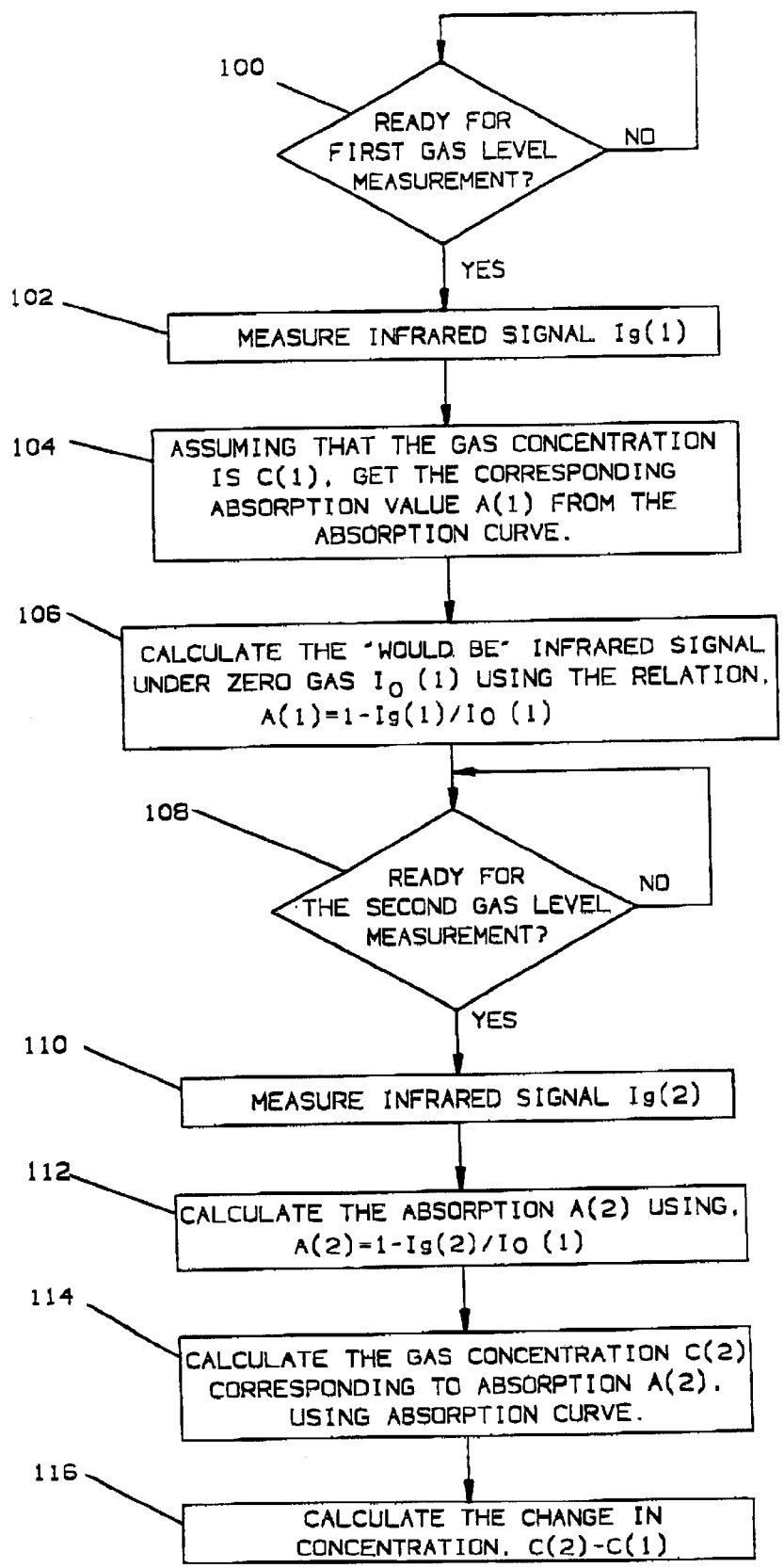
FIG. 4 is a flow chart relating to the method of the invention.

The method steps are illustrated in FIG. 4. At decision step 100 the routine cycles in a loop until the control is ready for the first gas level measurement. Infrared signal $I_g(1)$ is measured at process step 102. At step 104 the control assumes that the gas concentration is $C(1)$ and gets the corresponding absorption value $A(1)$ from the absorption curve in memory. Process step 106 calculates the infrared signal under zero gas $I_o(1)$, using the absorption value $A(1)$ obtained in step 104, and using the relation $A(1)=1-I_g(1)/I_o(1)$. Decision step 108 determines whether the control is ready for the second gas level measurement and when the response is positive the infrared signal $I_g(2)$ is measured. Step 112 calculates the absorption $A(2)$ using $A(2)=1-I_g(2)/I_o(1)$. In step 114, the gas concentration $C(2)$ corresponding to absorption $A(2)$ is calculated using the stored absorption curve and finally at 116 the change in concentration, $C(2)-C(1)$, is calculated.

The forced calibration scheme described above effectively reduces the error on concentration delta measurements without any re-calibration of the sensor. This is extremely beneficial for sensors that cannot be practically serviced and require long life. The forced calibration scheme can be used for any type of chemical/gas for which a rate of change or difference measurement is required.

It should be noted that although preferred embodiments of the invention have been described by way of illustrating the invention, the invention includes all modifications and equivalents of the disclosed embodiments falling within the scope of the appended claims.

What is claimed:

1. A sensor-based calibration method of measuring the change in concentration of a selected chemical in an environment with an infrared source for generating an infrared signal subjected to an optical absorption by the selected chemical, and using a non-linear infrared sensor having a microprocessor with a memory, the sensor measuring an infrared signal $I_g$ which decreases with increasing concentration of the selected chemical and in which an infrared absorption vs. chemical concentration curve information for the selected chemical is stored in the memory of the microprocessor and in which the microprocessor calculates an absorption in terms of an absorption value using a physical law of optical absorption based on the complementary relation between a measured chemical infrared signal and a resultant absorption:

$$Absorption = 1 - I_g/I_o$$

where $I_g$ is the measured chemical infrared signal and $I_o$ is an infrared signal corresponding to a baseline presence of the selected chemical the method minimizing errors caused by changes in calibration over time, comprising the steps of measuring a first signal $I_g(1)$, using an absorption value under a preselected chemical concentration value $C(1)$, calculating a $I_o(1)$ value, measuring a second signal $I_g(2)$ and calculating a second absorption value and a respective new concentration value $C(2)$ using $I_o(1)$ and $I_g(2)$ and subtracting $C(1)$ from $C(2)$ to obtain the change in concentration.

2. A method according to claim 1 in which the selected chemical is $C_2$ gas.

3. A method according to claim 2 in which the infrared absorption vs. gas concentration curve covers $CO_2$ concentrations at least between approximately 400 and 2000 ppm.

4. A method according to claim 3 in which the selected gas concentration value $C(1)$ used in calculating the $I_o(1)$ value is approximately 800 ppm.

5. A sensor-based calibration method of measuring the change in concentration level of a selected chemical in an environment using a non-linear infrared sensor having a microprocessor with a memory capable of storing infrared absorption versus chemical concentration curve information formed by a plurality of coordinate points defined by an abscissa and an ordinate, the sensor measuring a signal which is dependent upon concentration level of the selected chemical and in which related curve information for the selected chemical is stored in the memory of the microprocessor, the method minimizing errors caused by changes in calibration of the sensor over time, comprising the steps of measuring a pair of first and second signals of the selected chemical, with concentration level being the abscissa of the curve, assuming a selected first concentration level to obtain a corresponding ordinate in order to calculate, along with the first signal, a baseline selected chemical concentration value, calculating a second ordinate using the calculated baseline selected chemical concentration value along with the second signal which second ordinate is selected to a second concentration level, determining the related second concentration level and subtracting the first concentration level from the second concentration level to obtain the change in concentration.

6. A method according to claim 5 in which the sensor is a metal oxide sensor.

7. A method according to claim 6 in which the selected chemical is $CO_2$.

* * * * *